(12) United States Patent
Rockhill

(10) Patent No.: US 9,439,972 B2
(45) Date of Patent: Sep. 13, 2016

(54) ANTIFUNGAL SERUM

(71) Applicant: Turner Rockhill, Akron, OH (US)

(72) Inventor: Turner Rockhill, Akron, OH (US)

(73) Assignee: Ad Lunam Labs, Inc., Henderson, NV (US)

( * ) Notice: Subject to any disclaimer, the term of this patent is extended or adjusted under 35 U.S.C. 154(b) by 0 days.

(21) Appl. No.: 14/022,389

(22) Filed: Sep. 10, 2013

(65) Prior Publication Data

US 2014/0011871 A1    Jan. 9, 2014

Related U.S. Application Data

(60) Provisional application No. 61/698,875, filed on Sep. 10, 2012.

(51) Int. Cl.

| | | |
|---|---|---|
| *A61K 31/20* | (2006.01) | |
| *A61K 31/19* | (2006.01) | |
| *A61K 36/00* | (2006.01) | |
| *A61K 36/61* | (2006.01) | |
| *A61K 36/534* | (2006.01) | |
| *A61K 47/44* | (2006.01) | |
| *A61K 47/14* | (2006.01) | |
| *A61K 31/201* | (2006.01) | |
| *A61K 31/27* | (2006.01) | |
| *A61K 9/00* | (2006.01) | |
| *A61K 31/22* | (2006.01) | |
| *A61K 31/325* | (2006.01) | |
| *A61K 36/185* | (2006.01) | |

(52) U.S. Cl.
CPC ............. *A61K 47/44* (2013.01); *A61K 9/0014* (2013.01); *A61K 31/201* (2013.01); *A61K 31/22* (2013.01); *A61K 31/27* (2013.01); *A61K 31/325* (2013.01); *A61K 36/185* (2013.01); *A61K 47/14* (2013.01); *A61K 31/19* (2013.01); *A61K 31/20* (2013.01); *A61K 36/534* (2013.01); *A61K 36/61* (2013.01)

(58) Field of Classification Search
CPC ...... A61K 31/01; A61K 36/61; A61K 31/19; A61K 36/534
USPC .................. 514/558, 557; 424/742, 747, 725
See application file for complete search history.

(56) References Cited

U.S. PATENT DOCUMENTS

2005/0020678 A1 * 1/2005 Denton .......................... 514/546

OTHER PUBLICATIONS

Radhakrishna, "The best Natural Fungicides" (Mar. 2012).*
Windholz et al., The Merck Index, pp. 612, abstract No. 611; p. 9341, abstract No. 9347; and p. 9649, abstract No. 9650.*
Nenoff et al., "Antifungal Activity of the Essential Oil of Melaleuca alternifolia (Tea Tree Oil) against Pathogenic Fungi in vitro", Skin Pharmacology, vol. 9, No. 6, pp. 388-394 (1996).*
Edris et al., "Antifungal activity of peppermint and sweet basil essential oils and their major aroma constituents on some plant pathogenic fungi from the vapor base", Nahrung/Food, vol. 47, No. 2, pp. 117-121 (2003).*

* cited by examiner

*Primary Examiner* — Kevin E Weddington
(74) *Attorney, Agent, or Firm* — Alvin T. Rockhill

(57) ABSTRACT

The subject invention is based upon the discovery that an antifungal agent can be delivered through the fingernail or the toenail of an infected human to treat onychomycosis by dissolving or dispersing the antifungal agent in a solvent system which is comprised of a combination of an alkyl lactate and *Simmondsia chinesis* seed oil. In accordance with this invention the antifungal agent is absorbed by and incorporated into the nail matrix by diffusing through the epithelium of the nail bed to reach the nail bed hyperkeratosis. The antifungal agent additionally penetrates into the ventral surface of the nail plate. The subject invention more specifically discloses an antifungal serum which is comprised of (1) an alkyl lactate, such as isoamyl lactate, (2) *Simmondsia chinesis* seed oil, and (3) an antifungal agent, such as tolnaftate or undecylenic acid.

20 Claims, No Drawings

ANTIFUNGAL SERUM

This application claims the benefit of U.S. Provisional Patent Application Ser. No. 61/698,875 filed on Sep. 10, 2012. The teachings of U.S. Provisional Patent Application Ser. No. 61/698,875 are incorporated herein by reference in their entirety.

BACKGROUND OF THE INVENTION

A fungus is a member of a large group of organisms that includes microorganisms such as yeasts and molds, as well as the more familiar mushroom. These organisms are classified as a Kingdom, Fungi, which is separate from plants, animals and bacteria. Before the introduction of molecular methods for phylogenetic analysis, taxonomists considered fungi to be members of the Plant Kingdom primarily because of the similarities in lifestyle, as both fungi and plants are largely immobile, and have similarities in general morphology and growth habitat. Post molecular methods for phylogenetic analysis, the fungi have been a separate Kingdom distinct from both plants and animals, from which they appear to have diverged around one billion years ago. Advances in molecular genetics have opened the door for DNA analysis to be incorporated into taxonomy, which has oftentimes challenged the historical groupings of fungi based on morphology and other traits. Phylogenetic studies published in the last decade have helped reshape the classification of the Kingdom Fungi, which is divided into one subkingdom, seven phyla, and ten subphyla.

The fungus kingdom encompasses an enormous diversity of taxa with varied ecologies, life cycle strategies, and morphologies ranging from single-celled aquatic chytrids to large mushrooms. However, little is known of the true diversity of Kingdom Fungi, which has been estimated at around 1.5 million species, with about 5% of these having been formally classified.

The English word fungus is directly adopted from the Latin Fungus (mushroom), used in the writings of Florace and Pliny. This in turn is derived from the Greek word Sphongos (Sponge), which refers to the macroscopic structures and morphology of mushrooms and molds. The discipline of biology devoted to the study of fungi is known as mycology, which is regarded as a branch of botany, even though studies have shown that fungi are more closely related to animals than to plants.

The Kingdom Fungi includes some of the most important organisms, both in terms of their economic and ecological roles. For instance fungi by breaking down the dead organic material in the environment continue the cycle of nutrients through ecosystems. Furthermore, most vascular plants could not grow without the symbiotic fungi that inhabit their roots and supply essential nutrients. Fungi have been essential in providing many breakthrough drugs, such as penicillin and more sophisticated antibiotics. Other fungi have given us wonderful foods such as mushrooms, morels and the much desired truffle. From fungi we also obtain our breads, beers, and champagnes. However, with the Kingdom Fungi also comes the negative.

Fungi are also responsible for a number of diseases of both plant (leaf, root and stem rot, rusts and smuts) and varied diseases in animals and humans. Precisely because fungi are more genetically and chemically similar to animals than any other organisms, fungal diseases are very difficult to treat.

We now turn to one fungal problem in particular relating to human health. Onychomycosis is a fungal infection of the fingernail or toenail. Onychomycosis is a progressive, recurring fungal infection that initially first occurs in the nail bed and progresses to the nail plate. The main structural components of the nail include the lateral and proximal folds, cuticle, matrix, plate and hyponychium. The proximal nail fold is located at the proximal end of the visible nail plate where it folds over itself. The horny layer of the proximal nail fold is called the cuticle. The cuticle consists of modified stratum corneum that originates at the junction of the dorsal and ventral epithelial surfaces and proceeds along the nail surface. The cuticle protects the matrix from exposure to foreign material, including infection from microorganisms. The matrix is the growth center of the nail and is located at the proximal end under the cuticle. This site contains basal cells that migrate into the nail plate, where they divide and differentiate, forming the hard, keratinized component of the nail plate. The nail plate is the largest structure of the nail unit and is attached to the top of the nail bed. This transparent structure is gradually replaced as it grows out. The structure is completely renewed every 6 months on fingers and every 10 to 18 months on toes. The nail grows faster on longer digits, digits that are used most often and on traumatized nails. The nail bed is located under the nail plate and consists of epidermal grooves and ridges that contain small blood vessels. The dermis of the nail borders bone (the phalanx) rather than subcutaneous tissue.

Fungal infections usually invade the nail (between the nail plate and the nail bed) through an opening in the subungual space of the hyponychium, near the distal groove. The infection starts distally, then progresses proximally. However, trauma to the cuticle may also permit entry of fungal organisms.

The types of microorganisms that cause onychomycosis can be broadly classified into 2 groups: dermatophytes and nondermatophytes. Dermatophytes are fungi that infect keratinous tissue. Nondermatophytes that cause onochomycosis are either yeasts or molds. Dermatophytes are by far the most common causative pathogens of onychomycosis.

The nail provides the perfect place for the fungus and protects it while it grows, since fungi love damp, warm, dark places, the nails of our fingers and toes are very effective barriers. This barrier makes it quite difficult for a superficial infection to invade the nail. However, once an infection has invaded that same barrier that was so effective in protecting us against infection now works against us, making this type of fungal infection very difficult to treat.

Onychomycosis is not an uncommon disease. This type of infection accounts for approximately half of all nail disorders and one third of cutaneous fungal infections in the United States. Studies suggest that the number of persons affected is apparently on the rise. This rise may be attributed to many factors among them the aging population. Some studies suggest that 48% of the population may be infected by age 70. The increasingly higher occurrence of onychomyosis may also be attributable to the greater use of immunosuppressive drugs, the increasing number of people infected with HIV, the increasing exposure to pathogens in public swimming pools and spas, and high heels and tight fitting shoes in fashion styles. The growth of low cost nail salons that may not always properly disinfect nail instruments thoroughly between clients is also attributing to the increasing occurrence of onychomycosis in many countries.

The problem with onychomycosis is aggravated by the fact that it is very contagious and easily passed from person to person. In fact, many infected people are under the impression that the infection will resolve spontaneously and go without any treatment while infecting other people. On the other hand, onychomycosis is notoriously difficult to treat and long treatment periods have typically been required to cure the infection using conventional drugs and techniques. It is not uncommon for patients to simply give up before that infection has been eradicated.

The dermatophyte fungus that causes the onychomycosis infection is ubiquitous. It rarely remits spontaneously and typically spreads to involve the entire nail anatomy. Unfortunately, onychomycosis frequently spreads to other digits, and sometimes spreads to other sites and to other family members as well as others that come in contact with the infected person or infected articles which are contaminated by the infected person.

Participants in numerous athletic activities of varied nature are much more susceptible to onychomycosis. Some of these athletic activities include: long distance running, ballet dancing, golf, and soccer. A wide array of preexisting medical conditions also leads to a higher level of susceptibility to being infected with onychomycosis. Some of these medical conditions include: diabetes mellitus, blood circulation disorders (including varicose veins in the legs, pallor of fingers and toes, and poor peripheral circulation), and genetic susceptibility associated with Down's syndrome, Raynaud syndrome, and Cushing's syndrome. Cancer patients that are being treated with chemotherapy and organ transplant recipients on anti-rejection drugs are also in a high risk group.

Nail trauma is a frequent cause of onychomycosis. Individuals in trades and professions that involve the wearing of sports or safety shoes are also at higher risk. Men are more prone to onychomycosis than women. The reasons for this gender difference are not clear but may involve higher occurrence of nail trauma that results from professional and athletic activities. Social and/or genetic factors may also play a role.

Nail fungus is more than just a cosmetic problem. Many people complain of discomfort in walking, pain, or limitation of their work or other activities. Gross distortion and dystrophy of the nail may cause trauma to adjacent skin and may lead to secondary bacterial infection. In several studies, patients with onochomycosis reported significantly poorer general health, mental health, social functioning, and body pain than did people without this nail infection. Psychosocial limitations included fear of social situations that exposed on infected fingernail or toenail.

In immuno-compromised people, there is a great risk that this infection will disseminate. Although onychomycosis causes some degree of morbidity for healthy individuals it is especially pronounced in high risk patients such as diabetics, patients with HIV, AIDS or other types of immunosuppressant, including transplant recipients, and patients on long term corticosteroid therapy.

Onychomycosis poses a greater risk to diabetic patients because of the possible sequelae. In particular, high risk diabetic patients with compromised lower extremities and severe neuropathy are at increased risk of developing complications from onychomycosis. Most notably impaired sensation can make many diabetics less aware of minor abrasions and ulcerations on their feet that may be caused by trauma, from poor nail grooming or by the sharp brittle or infected nails characteristic of onychomyosis. These lesions in turn may develop into serious paronychia, cellulites or bacterial infections, and contribute to the severity of the diabetic foot. Osteomyelitis can also result from neglected, infected nail bed erosion in diabetic patients because of the close proximity of the nail bed to the underlying bone. Nearly 18% of gangrene and 10% of foot ulcers in people can be attributed to onychomycosis. Thus, diabetics with onychomycosis should treat it quickly as it may lead to much greater, catastrophic results.

Everyone should seek treatment of a nail fungus as soon as one is suspected. Symptoms of nail fungus can include nail changes such as, brittleness, change in nail shape, crumbling of the outside edges of the nail, debris trapped under the nail, loosening or lifting up of the nail, loss of luster or shine, white spots, thickening of the nail or white or yellow streaks on the side of the nail. Much more rarely, a black strip or spot is present.

Current treatment for ocychomycosis include mechanical debridement, oral drugs, topical drugs, removal of nail and laser treatments. Mechanical debridement is a traditional podiatric approach that requires time, specialized instruments, and experience. The goal of this approach is to reduce pressure and fungal load by mechanically reducing nail thickness. Since mechanical debridement removes a large portion of fungal material it has potential to enhance the effectiveness of other therapies. However, it does have its limitations. It does not eradicate the infectious pathogens, and it must be repeated as the nail grows until the infection is gone.

Oral antifungal medications are often prescribed as first-line treatments for nail fungus. These systemic drugs reach the infected nail via the peripheral circulation. Though antifungal medications have improved it has been suggested that as many as 25% to 40% of onychomycosis cases are classified as treatment failures in clinical practice. In addition these oral drugs have many adverse side affects including headache, gastrointestinal symptoms such as diarrhea, dyspepsia, abdominal pain, constipation, nausea and flatulence; dermatological symptoms such as rash, pruritus and urticaria. Additionally these oral antifungal drugs may affect the liver, therefore liver function and white cell counts should be assessed at baseline and periodically during treatment. Neutropenia and transient taste disturbance may also result. Another downside to oral antifungal medication is the financial impact for the patient as these oral antifungal drugs can be quite expensive.

Current topical antifungal therapy is effective for the treatment of onochomycossis in some cases. This approach involves the direct application of an antifungal drug to the infected nail. These drugs are thought to diffuse through the nail plate to reach the site of infection, where they eradicate fungal organisms. These over the counter creams and ointments generally do not help treat this condition.

Removal of the nail involves the removal of the affected nail plate; this may be performed surgically or chemically. This approach allows growth of a new nail but can traumatize the nail bed, which may affect the appearance of the new nail. Total nail removal causes great discomfort to the patient and therefore is discouraged. Only in the most severe cases should this method be recommended.

Practitioners have been using lasers for toenail fungus since 2009. However, podiatrists using this method disagree greatly on its effectiveness both medically and from the standpoint of cost. The treatment consists of the practitioner aiming a laser beam at the patient's toenail to kill the organisms that cause the fungus. The nails are not immediately clear after the treatment, which takes up to an hour and the patient must wait for the fungus free nail to grow out which can take up to about 18 months. Multiple laser treatments are frequently required and the total cost of such treatments can preclude them from being a possibility for many patients. In addition to this the high cost of laser treatments is generally not covered by insurance because it is considered to be an aesthetic procedure.

Considering the problems associated with the current methods of treatment for nail fungus something more ideal needs to be found. Georgeanne Botek, DPM Department of Orthopedic Surgery at The Cleveland Clinic, suggests that the ideal anti fungal treatment would be broad spectrum, taken up and incorporated into the nail matrix, diffusing through the epithelium of the nail bed to reach the nail bed hyperkeratosis, and penetrating into the ventral surface of the plate. Additionally, it would be effective, with high rates of clinical cure (ascertained by laboratory testing, fungal culture) and a low rate of relapse and effective when used short term (the duration of new nail re-growth) and have few in any adverse effects and adverse drug interactions. It should also, of course, be cost effective.

SUMMARY OF THE INVENTION

The subject invention is based upon the discovery that an antifungal agent can be delivered through the fingernail or the toenail of an infected human to treat onychomycosis by dissolving or dispersing the antifungal agent in a solvent system which is comprised of a combination of an alkyl lactate and Simmondsia chinesis seed oil. It is critical for the solvent system to contain both the alkyl lactate and Simmondsia chinesis seed oil to attain penetration through the fingernail or the toenail. In other words, for effective delivery of the antifungal agent through the nail to reach the fungus under the nail it is critical for the antifungal agent to be dissolved or dispersed in a mixture of an alkyl lactate and *Simmondsia chinesis* seed oil. Accordingly, in accordance with this invention the antifungal agent is absorbed by and incorporated into the nail matrix by diffusing through the epithelium of the nail bed to reach the nail bed hyperkeratosis. The antifungal agent additionally penetrates into the ventral surface of the nail plate.

The antifungal serum of this invention has been determined to be highly effective (offers a high rate of clinical cure) and offers a low rate of relapse. It is also effective when used short term (the duration of new nail re-growth) and is not believed to have any adverse effects or to cause adverse drug interactions. Additionally, the antifungal serum of this invention is highly cost effective in treating onychomycosis.

The subject invention more specifically discloses an antifungal serum which is comprised of (1) an alkyl lactate, wherein the alkyl group in the alkyl lactate contains from 2 to about 12 carbon atoms, (2) *Simmondsia chinesis* seed oil, and (3) an antifungal agent.

The present invention also reveals a method for treating a human fingernail or toenail which is infected with onychomycosis which comprised applying an antifungal serum to the infected nail, wherein the antifungal serum is comprised of (1) an alkyl lactate, wherein the alkyl group in the alkyl lactate contains from 2 to about 12 carbon atoms, (2) *Simmondsia chinesis* seed oil, and (3) an antifungal agent.

DETAILED DESCRIPTION OF THE INVENTION

The antifungal agent of this invention is comprised of (1) an alkyl lactate, (2) *Simmondsia chinesis* seed oil, and (3) an antifungal agent. The alkyl lactate utilized will typically have an alkyl group that contains from 2 to about 12 carbon atoms and will accordingly be of the structural formula:

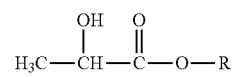

wherein R represents an straight chained or a branched alkyl group that contains from 2 to 12 carbon atoms. The alkyl group (R) of the alkyl lactate will typically contain from 2 to about 8 carbon atoms and will more typically contain from 3 to 6 carbon atoms. In many cases the alkyl group of the alkyl lactate will contain from 4 to 6 carbon atoms. For instance, the alkyl group of the alkyl lactate can contain 4, 5, or 6 carbon atoms. Some representative examples of alkyl lactates that can be used include: ethyl lactate, n-propyl lactate, iso-propyl lactate, n-butyl lactate, iso-butyl lactate, t-butyl lactate, isoamyl lactate, n-pentyl lactate, t-pentyl lactate, n-hexyl lactate, iso-hexyl lactate, t-hexyl lactate, n-heptyl lactate, iso-heptyl lactate, t-heptyl lactate, n-octyl lactate, iso-octyl lactate, and t-octyl lactate.

Isoamyl lactate is preferred for utilization as the alkyl lactate because it is not a volatile as the lower molecular weight alkyl lactates, but is still a low viscosity liquid at room temperature. Isoamyl lactate is of the structural formula:

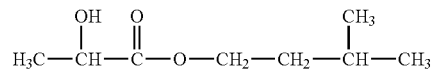

and is also a colorless liquid having a pleasant mild odor. Isoamyl lactate is preferred for utilization in conjunction with oil soluble antifungal agents, such as undecylenic acid.

Mixtures of various alkyl lactates can be utilized in the antifungal serum of this invention. For instance, a mixture of ethyl lactate and isoamyl lactate can be employed. Ethyl lactate is a colorless liquid of the structural formula:

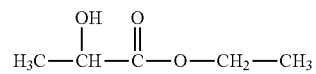

which is preferred for utilization in conjunction with antifungal agents which are water soluble. However, ethyl lactate has a strong odor. Accordingly, it is preferred to utilize ethyl lactate in mixtures with a higher molecular weight alkyl lactate to reduce volatility and the level of odor. It is desirable to utilize ethyl lactate in mixtures with isoamyl lactate in some cases. The weight ratio of ethyl lactate to isoamyl lactate will typically be within the range of about 1:10 to about 20:1. The weight ratio of ethyl lactate to isoamyl lactate will more typically be within the range of about 1:5 to about 10:1. Such mixtures of ethyl lactate and isoamyl lactate will preferably contain from about 30 weight percent to 70 weight percent ethyl lactate and from about 30 weight percent to about 70 weight percent isoamyl lactate. Such mixtures of ethyl lactate and isoamyl lactate will more preferably contain from about 40 weight percent to 60 weight percent ethyl lactate and from about 40 weight percent to about 60 weight percent isoamyl lactate. Such mixtures of ethyl lactate and isoamyl lactate will most preferably contain from about 45 weight percent to 55 weight percent ethyl lactate and from about 45 weight percent to about 55 weight percent isoamyl lactate.

The *Simmondsia chinesis* seed oil used in the antifungal serums of this invention is commonly known as jojoba oil or goat-nut oil. The *Simmondsia chinesis* seed oil can be expeller processed or it can be cold pressed at a temperature which does not exceed 150° F. (66° C.) and which preferably does not exceed 120° F. (49° C.). The *Simmondsia chinesis* seed oil is preferably golden *Simmondsia chinesis* seed oil which is filtered, but which is not refined. Accordingly, the *Simmondsia chinesis* seed oil will normally be filtered to remove undesired particulate matter. In some cases refined *Simmondsia chinesis* seed oil can by used in the antifungal serums of this invention with good results. Such refined *Simmondsia chinesis* seed oil is clear, rather than being golden in color, and offers the advantage of having an extended shelf-life without becoming rancid. However, in the practice of the subject invention color is not of importance and oil stabilization can be achieved by adding a small amount of a soluble antioxidant, such as Vitamin E to the antifungal serum. In any case, the *Simmondsia chinesis* seed oil can be refined by extracting it from unrefined material with an organic solvent, such as n-hexane or cyclohexane, and then fractionally distilling the extract to remove the organic solvent.

In cases where Vitamin E ($\alpha$-tocopherol, $\beta$-tocopherol, $\gamma$-tocopherol, and/or $\delta$-tocopherol) is utilized in the antifungal serum it is typically present at a level which is within the range of about 0.01 weight percent to about 2 weight percent, based upon the total weight of the antifungal serum. In cases where Vitamin E is utilized in the antifungal serum it is more typically added at a level which is within the range of 0.05 weight percent to about 1 weight percent, and is generally employed at a level which is within the range of 0.1 weight percent to 0.5 weight percent, based upon the total weight of the antifungal serum.

A wide variety of antifungal agents can be utilized in the antifungal serums of this invention. For instance, the antifungal agent can be selected from azoles or imidazoles, including but not limited to, miconazole, econazole, terconazole, saperconazole, itraconazole, butaconazole, clotrimazole, tioconazole, fluconazole and ketoconazole, vericonazole, fenticonazole, sertaconazole, posaconazole, bifonazole, oxiconazole, sulconazole, elubiol, vorconazole, isoconazole, flutrimazole, tioconazole and their pharmaceutically acceptable salts and the like. The antifungal agent can also be an allylamine or it can be selected from other chemical families, including but not limited to, ternafine, naftifine, amorolfine, butenafine, ciclopirox, griseofulvin, undecyclenic acid, haloprogin, tolnaftate, nystatin, iodine, rilopirox, BAY 108888, purpuromycin and their pharmaceutically acceptable salts. However, the preferred antifungal agents for utilization in conjunction with this invention include clioquinol, haloprogin, miconazole nitrate, poridone-iodine, tolnaftate, undecylenic acid, calcium undecylenate, cobalt undecylenate, zinc undecylenate, and clotrimazole. Undecylenic acid is a highly preferred antifungal agent for utilization in the practice of this invention.

The alkyl lactate will typically be present in the antifungal serums of this invention at a level which is within the range of about 5 weight percent to about 80 weight percent and will more typically be present at a level which is within the range of about 10 weight percent to about 70 weight percent. The alkyl lactate will commonly be present in the antifungal serums of this invention at a level which is within the range of about 10 weight percent to about 60 weight percent and will more commonly be present at a level which is within the range of about 15 weight percent to about 60 weight percent. In most cases, the alkyl lactate will typically be present in the antifungal serums of this invention at a level which is within the range of about 15 weight percent to about 50 weight percent.

The *Simmondsia chinesis* seed oil will typically be present in the antifungal serums of this invention at a level which is within the range of f about 5 weight percent to about 80 percent and more typically be present at a level which is within the range of about 10 weight percent to about 70 percent. The *Simmondsia chinesis* seed oil will commonly be present in the antifungal serums of this invention at a level which is within the range of about 10 weight percent to about 60 percent and more typically will be present at a level which is within the range of about 15 weight percent to about 50 percent. In most cases, the *Simmondsia chinesis* seed oil will be present in the antifungal serums of this invention at a level which is within the range of about 15 weight percent to about 45 percent and in many cases will preferably be present at a level which is within the range of about 15 weight percent to about 40 percent.

The antifungal agent will typically be present at a level of about 0.25 weight percent to about 40 weight percent and will more typically be present at a level which is within the range of about 0.5 weight percent to about 35 weight percent. The antifungal agent will commonly be present at a level of about 0.75 weight percent to about 30 weight percent and will more commonly be present at a level which is within the range of about 1 weight percent to about 30 weight percent. However, the level of antifungal agent utilized is highly dependant upon the identity of the antifungal agent employed in the antifungal serum. For instance, undecylenic acid, calcium undecylenate, cobalt undecylenate, zinc undecylenate will typically be utilized alone or in a mixture at a level which is within the range of about 5 weight percent to about 30 weight percent. Undecylenic acid, calcium undecylenate, cobalt undecylenate, zinc undecylenate will more typically be utilized alone or in a mixture at a level which is within the range of about 10 weight percent to about 25 weight percent. Undecylenic acid, calcium undecylenate, cobalt undecylenate, zinc undecylenate will most typically be utilized alone or in a mixture at a level which is within the range of about 15 weight percent to about 25 weight percent. Undecylenic acid, calcium undecylenate, cobalt undecylenate, zinc undecylenate will preferably be utilized alone or in a mixture at a level which is within the range of about 20 weight percent to about 25 weight percent.

In cases where haloprogin, tolnaftate, or clotrimazole are utilized as the antifungal agent in the antifungal serums of this invention they will typically be incorporated at a level which is within the range of about 0.25 weight percent to about 2 weight percent. Haloprogin, tolnaftate, or clotrimazole will more typically be incorporated into the antifungal serums of this invention at a level which is within the range of about 0.5 weight percent to about 1.5 weight percent and will preferably be included at a level of which is within the range of about 0.75 weight percent to about 1.25 weight percent. It is normally most preferred for haloprogin, tolnaftate, or clotrimazole to be included in the antifungal serums of this invention at a level of 1 weight percent.

In cases where poridone-iodine is utilized as the antifungal agent in the antifungal serums of this invention it will typically be incorporated at a level which is within the range of about 4 weight percent to about 20 weight percent. Poridone-iodine will more typically be incorporated into the antifungal serums of this invention at a level which is within the range of about 6 weight percent to about 14 weight percent and will preferably be included at a level of which is within the range of about 8 weight percent to about 12 weight percent. It is normally most preferred for poridone-iodine to be included in the antifungal serums of this invention at a level of 10 weight percent.

In cases where miconazole nitrate is utilized as the antifungal agent in the antifungal serums of this invention it will typically be incorporated at a level which is within the range of about 0.5 weight percent to about 8 weight percent. Miconazole nitrate will more typically be incorporated into the antifungal serums of this invention at a level which is within the range of about 1 weight percent to about 4 weight percent and will preferably be included at a level of which is within the range of about 1.5 weight percent to about 3 weight percent. It is normally most preferred for miconazole nitrate to be included in the antifungal serums of this invention at a level of 2 weight percent.

In cases where clioquinol is utilized as the antifungal agent in the antifungal serums of this invention it will typically be incorporated at a level which is within the range of about 1 weight percent to about 10 weight percent. Clioquinol will more typically be incorporated into the antifungal serums of this invention at a level which is within the range of about 2 weight percent to about 4 weight percent and will preferably be included at a level of which is within the range of about 2.5 weight percent to about 3.5 weight percent. It is normally most preferred for clioquinol to be included in the antifungal serums of this invention at a level of 3 weight percent.

In one embodiment of this invention the alkyl lactate is present in the antifungal serum of this invention at a level which is within the range of about 15 weight percent to about 40 weight percent, wherein the Simmondsia chinesis seed oil is present at a level of about 15 weight percent to about 40 percent, wherein the an antifungal agent is at least one member selected from the group consisting of undecylenic acid, calcium undecylenate, cobalt undecylenate, zinc undecylenate present, and wherein the antifungal agent is present at a level of about 20 weight percent to about 25 weight percent.

In another embodiment of this invention the alkyl lactate is present in the antifungal serum of this invention at a level which is within the range of about 15 weight percent to about 40 weight percent, wherein the *Simmondsia chinesis* seed oil is present at a level of about 15 weight percent to about 40 percent, wherein the an antifungal agent is at least one member selected from the group consisting of undecylenic acid, calcium undecylenate, cobalt undecylenate, zinc undecylenate present, and wherein the antifungal agent is present at a level of about 20 weight percent to about 25 weight percent.

In a further embodiment of this invention the alkyl lactate is present in the antifungal serum of this invention at a level which is within the range of about 15 weight percent to about 35 weight percent, wherein the *Simmondsia chinesis* seed oil is present at a level of about 15 weight percent to about 35 percent, wherein the an antifungal agent is at least one member selected from the group consisting of undecylenic acid, calcium undecylenate, cobalt undecylenate, zinc undecylenate present, and wherein the antifungal agent is present at a level of about 20 weight percent to about 25 weight percent.

In a further embodiment of this invention the alkyl lactate is present in the antifungal serum of this invention at a level which is within the range of about 15 weight percent to about 30 weight percent, wherein the *Simmondsia chinesis* seed oil is present at a level of about 15 weight percent to about 30 percent, wherein the an antifungal agent is at least one member selected from the group consisting of undecylenic acid, calcium undecylenate, cobalt undecylenate, zinc undecylenate present, and wherein the antifungal agent is present at a level of about 20 weight percent to about 25 weight percent.

In still another embodiment of this invention the alkyl lactate is present in the antifungal serum of this invention at a level which is within the range of about 15 weight percent to about 25 weight percent, wherein the *Simmondsia chinesis* seed oil is present at a level of about 15 weight percent to about 25 percent, wherein the an antifungal agent is at least one member selected from the group consisting of undecylenic acid, calcium undecylenate, cobalt undecylenate, zinc undecylenate present, and wherein the antifungal agent is present at a level of about 20 weight percent to about 25 weight percent.

In another embodiment of this invention the alkyl lactate is present in the antifungal serum of this invention at a level which is within the range of about 20 weight percent to about 80 weight percent, the *Simmondsia chinesis* seed oil is present at a level of about 20 weight percent to about 80 percent, and the antifungal agent is selected from the group consisting of haloprogin, tolnaftate, or clotrimazoleand is present at a level which is within the range of about 0.25 weight percent to about 2 weight percent. In such compositions it is typically preferred for the alkyl lactate to be present in the antifungal serum at a level which is within the range of about 20 weight percent to about 80 weight percent, for the *Simmondsia chinesis* seed oil to be present at a level of about 20 weight percent to about 80 percent, and for the antifungal selected from the group consisting of haloprogin, tolnaftate, or clotrimazoleand to be present at a level which is within the range of about 0.5 weight percent to about 1.5 weight. In such compositions it is typically more preferred for the alkyl lactate to be present in the antifungal serum at a level which is within the range of about 20 weight percent to about 80 weight percent, for the *Simmondsia chinesis* seed oil to be present at a level of about 20 weight percent to about 80 percent, and for the antifungal selected from the group consisting of haloprogin, tolnaftate, or clotrimazoleand to be present at a level which is within the range of about 0.75 weight percent to about 1.75 weight. In such compositions it is typically most preferred for the alkyl lactate to be present in the antifungal serum at a level which is within the range of about 20 weight percent to about 80 weight percent, for the *Simmondsia chinesis* seed oil to be present at a level of about 20 weight percent to about 80 percent, and for the antifungal selected from the group consisting of haloprogin, tolnaftate, or clotrimazoleand to be present at a level of about 1 weight percent. The antifungal agent use in such antifungal serums will typically consist solely of tolnaftate at a level of 1 weight percent.

The antifungal serum can also include a wide variety of other oils. These additional oils are typically vegetable oils, such as peppermint oil and/or tea tree oil. Peppermint oil can optionally be included at a level which is within the range of about 5 weight percent to about 45 weight percent and is typically included at a level which is within the range of about 5 weight percent to about 40 weight percent. Peppermint oil is commonly included at a level which is within the range of about 10 weight percent to about 35 weight percent and is more commonly included at a level which is within the range of about 15 weight percent to about 30 weight percent. Peppermint oil is preferably included in the antifungal serums of this invention at a level which is within the range of about 15 weight percent to about 25 weight percent.

Tea tree oil can optionally be included at a level which is within the range of about 5 weight percent to about 45 weight percent and is typically included at a level which is within the range of about 5 weight percent to about 40 weight percent. Tea tree oil is commonly included at a level which is within the range of about 10 weight percent to about 35 weight percent and is more commonly included at a level which is within the range of about 15 weight percent to about 30 weight percent. Tea tree oill is preferably included in the antifungal serums of this invention at a level which is within the range of about 15 weight percent to about 25 weight percent.

In one embodiment of this invention the additional oil is a combination of peppermint oil and tea tree oil, wherein the peppermint oil is present at a level which is within the range of about 5 weight percent to about 45 weight percent, and wherein the peppermint oil is present at a level which is within the range of about 5 weight percent to about 45 weight percent. In another embodiment of this invention the additional oil is a combination of peppermint oil and tea tree oil, wherein the peppermint oil is present at a level which is within the range of about 5 weight percent to about 40 weight percent, and wherein the peppermint oil is present at a level which is within the range of about 5 weight percent to about 40 weight percent.

In a further embodiment of this invention the additional oil is a combination of peppermint oil and tea tree oil, wherein the peppermint oil is present at a level which is within the range of about 10 weight percent to about 35 weight percent, and wherein the peppermint oil is present at a level which is within the range of about 10 weight percent to about 35 weight percent. In still another embodiment of this invention the additional oil is a combination of peppermint oil and tea tree oil, wherein the peppermint oil is present at a level which is within the range of about 15 weight percent to about 30 weight percent, and wherein the peppermint oil is present at a level which is within the range of about 15 weight percent to about 30 weight percent. In a preferred embodiment of this invention the additional oil additional oil is a combination of peppermint oil and tea tree oil, wherein the peppermint oil is present at a level which is within the range of about 15 weight percent to about 25 weight percent, and wherein the peppermint oil is present at a level which is within the range of about 15 weight percent to about 25 weight percent.

A highly preferred antifungal serum which utilizes undecylenic acid as its antifungal agent is comprised of isoamyl lactate which is present at a level which is within the range of about 15 weight percent to about 30 weight percent, *Simmondsia chinesis* seed oil which is present at a level of about 15 weight percent to about 30 weight percent, undecylenic acid which is present at a level with is within the range of about 15 weight percent to about 30 weight percent, the peppermint oil which is present at a level which is within the range of about 15 weight percent to about 30 weight percent, and tea tree oil which is present in the at a level which is within the range of about 15 weight percent to about 30 weight percent. In such formulations the isoamyl lactate will typically be present at a level which is within the range of about 15 weight percent to about 25 weight percent, the *Simmondsia chinesis* seed oil will typically be present at a level of about 15 weight percent to about 25 weight percent, the undecylenic acid will typically be present at a level with is within the range of about 20 weight percent to about 30 weight percent, the peppermint oil will typically be present at a level which is within the range of about 15 weight percent to about 25 weight percent, and the tea tree oil will typically be present in the at a level which is within the range of about 15 weight percent to about 25 weight percent. In such formulations the isoamyl lactate will more typically be present at a level which is within the range of about 18 weight percent to about 22 weight percent, the *Simmondsia chinesis* seed oil will more typically be present at a level of about 18 weight percent to about 22 weight percent, the undecylenic acid will more typically be present at a level with is within the range of about 23 weight percent to about 27 weight percent, the peppermint oil will more typically be present at a level which is within the range of about 18 weight percent to about 22 weight percent, and the tea tree oil will more typically be present in the at a level which is within the range of about 18 weight percent to about 22 weight percent. In such formulations the isoamyl lactate will generally be present at a level which is within the range of about 18 weight percent to about 20 weight percent, the *Simmondsia chinesis* seed oil will generally be present at a level of about 18 weight percent to about 20 weight percent, the undecylenic acid will generally be present at a level with is within the range of about 24 weight percent to about 26 weight percent, the peppermint oil will generally be present at a level which is within the range of about 18 weight percent to about 20 weight percent, and the tea tree oil will generally be present in the at a level which is within the range of about 18 weight percent to about 20 weight percent.

Another preferred antifungal serum which utilizes tolnaftate as its antifungal agent is comprised of isoamyl lactate which is present at a level which is within the range of about 15 weight percent to about 40 weight percent, *Simmondsia chinesis* seed oil which is present at a level of about 15 weight percent to about 40 weight percent, tolnaftate which is present at a level with is within the range of about 0.25 weight percent to about 2 weight percent, peppermint oil which is present at a level which is within the range of about 15 weight percent to about 40 weight percent, and tea tree oil which is present in the at a level which is within the range of about 15 weight percent to about 40 weight percent. In such formulations the isoamyl lactate is typically present at a level which is within the range of about 15 weight percent to about 30 weight percent, the *Simmondsia chinesis* seed oil is typically present at a level of about 15 weight percent to about 30 weight percent, the tolnaftate is typically present at a level with is within the range of about 0.5 weight percent to about 1.5 weight percent, the peppermint oil is typically present at a level which is within the range of about 15 weight percent to about 30 weight percent, and the tea tree oil is present is typically present the at a level which is within the range of about 15 weight percent to about 30 weight percent. In such formulations the isoamyl lactate is more typically present at a level which is within the range of about 20 weight percent to about 35 weight percent, the *Simmondsia chinesis* seed oil is more typically present at a level of about 20 weight percent to about 35 weight percent, the tolnaftate is more typically present at a level with is within the range of about 0.75 weight percent to about 1.25 weight percent, the peppermint oil is more typically present at a level which is within the range of about 20 weight percent to about 35 weight percent, and the tea tree oil is more typically present in the at a level which is within the range of about 20 weight percent to about 35 weight percent. In such formulations the isoamyl lactate is normally present at a level which is within the range of about 20 weight percent to about 30 weight percent, the *Simmondsia chinesis* seed oil is normally present at a level of about 20 weight percent to about 30 weight percent, the tolnaftate is normally present at a level with is within the range of about 0.75 weight percent to about 1.25 weight percent, the peppermint oil is normally present at a level which is within the range of about 20 weight percent to about 30 weight percent, and the tea tree oil is normally present in the at a level which is within the range of about 20 weight percent to about 30 weight percent. In such antifungal serum formulations the isoamyl lactate is generally present at a level which is within the range of about 22 weight percent to about 28 weight percent, the *Simmondsia chinesis* seed oil is generally present at a level of about 22 weight percent to about 28 weight percent, the tolnaftate is generally present at a level with is within the range of about 0.75 weight percent to about 1.25 weight percent, the peppermint oil is generally present at a level which is within the range of about 22 weight percent to about 28 weight percent, and the tea tree oil is generally present in the at a level which is within the range of about 22 weight percent to about 28 weight percent.

Other oils that may be used in antifungal serums of this invention include mineral oils (liquid petroleum jelly), oils of plant origin, oils of animal origin (lanolin), synthetic oils (perhydrosqualene), and silicone oils (cyclomethicone). The vegetable oils that can be included in the antifungal agents of this invention include avocado oil, soybean oil, coconut oil, shea butter, almond oil, eucalyptus essential oil, olive oil, hazelnut oil, walnut oil, peanut oil, corn oil, caster oil, soy oil, canola oil, rapeseed oil, cottonseed oil, palm oil, sesame oil, sunflower oil, safflower oil, rice bran oil, borage seed oil, syzigium aromaticum oil, hempseed oil, flaxseed oil, rape seed oil, evening primrose oil, rosehip oil, and melaleuca oil. Some representative examples of animal based oils that can optionally be utilized include various fish oils, such as herring oil, cod-liver oil, and salmon oil. Typically, the antifungal agents of this invention will be void of these additional oils since they are not believed to serve any beneficial purpose and dilute the levels of more desirable oils, such as peppermint oil, tea tree oil, and *Simmondsia chinesis* seed oil. Accordingly, in cases where such oil are included in the antifungal serum their total level will normally be limited to be within the range of 0 weight percent to about 25 weight percent and will more typically be limited to be within the range of 0 weight percent to 10 weight percent, based upon the total weight of the antifungal serum. In cases where such additional oils are included they will normally be present in a total amount which is within the range of about 1 weight percent to about 5 weight percent.

Fatty alcohols (cetyl alcohol), fatty acids, petrolatum, and waxes (carnauba wax or ozokerite) can also optionally be included in the antifungal agents of this invention. Petrolatum or mineral oil components, which when selected will generally be USP or NF grade. The petrolatum may be white or yellow. The viscosity or consistency grade of petrolatum is not narrowly critical. Petrolatum can be partially replaced with mixtures of hydrocarbon materials, which can be formulated to resemble petrolatum in appearance and consistency. For example, mixtures of petrolatum or mineral oil with different waxes and the like may be combined. Preferred waxes include bayberry wax, candelilla wax, ceresin, jojoba butter, lanolin wax, montan wax, ozokerite, polyglyceryl-3-beeswax, polyglyceryl-6-pentastearate, microcrystalline wax, paraffin wax, isoparaffin, vaseline solid paraffin, squalene, oligomer olefins, beeswax, synthetic candelilla wax, synthetic carnauba, synthetic beeswax and the like may be blended together. Typically, the antifungal agents of this invention will be void of petrolatum and waxes since they are not believed to serve any beneficial purpose and dilute the levels of more desirable oils, such as peppermint oil, tea tree oil, and *Simmondsia chinesis* seed oil. Accordingly, in cases where petrolatum and/or waxes are included in the antifungal serum their total level will normally be limited to be within the range of 0 weight percent to about 25 weight percent and will more typically be limited to be within the range of 0 weight percent to 10 weight percent, based upon the total weight of the antifungal serum. In cases where petrolatum and/or such waxes are included they will normally be present in a total amount which is within the range of about 1 weight percent to about 5 weight percent.

Antimicrobial agents that may be used in the antifungal serums of this invention. Some representative examples of antimicrobial agents that can be use include 2,4,4'-trichloro-2'-hydroxydiphenyl ether (or triclosan), 3,4,4'-trichlorobanilide, phenoxyethanol, phenoxypropanol, phenoxyisopropanol, hexamidine isethionate, metronidazole and its salts, miconazole and its salts, itraconazole, terconazole, econazole, ketoconazole, saperconazole, fluconazole, clotrimazole, butoconazole, oxiconazole, sulfaconazole, sulconazole, terbinafine, ciclopirox, ciclopiroxolamine, undecylenic acid and its salts, benzoyl peroxide, 3-hydroxybenzoic acid, 4-hydroxybenzoic acid, phytic acid, N-acetyl-L-cysteine acid, lipoic acid, azelaic acid and its salts, arachidonic acid, resorcinol, 2,4,4'-trichloro-2'-hydroxydiphenyl ether, 3,4,4'-trichlorocarbanilide, octopirox, octoxyglycerine, octanoylglycine, caprylyl glycol, 10-hydroxy-2-decanoic acid, dichlorophenyl imidazole dioxolane and its derivatives, described in patent WO 93/18743, farnesol and phytosphingosines, and mixtures thereof. The preferred antibacterial agents are triclosan, phenoxyethanol, octoxyglycerine, octanoylglycine, 10-hydroxy-2-decanoic acid, caprylyl glycol, farnesol and azelaic acid. By way of example, the antimicrobial agent may be used in the antifungal serums of this invention in an amount representing from 0.1% to 20% and preferably from 0.1% to 10% relative to the total weight of the antifungal serum.

The antifungal serums of this invention can optionally further contain an agent for stimulating the synthesis of dermal or epidermal macromolecules and/or for preventing their degradation. Among the active agents for stimulating dermal macromolecules or for preventing their degradation, mention may be made of those that act: either on collagen synthesis, such as extracts of *Centella asiatica*; asiaticosides and derivatives; ascorbic acid or vitamin C and its derivatives; synthetic peptides such as lamin, biopeptide CL or the palmitoyloligopeptide sold by the company Sederma; peptides extracted from plants, such as the soybean hydrolysate sold by the company Coletica under the trade name Phytokine®; and plant hormones such as auxins and lignans; or on elastin synthesis, such as the extract of *Saccharomyces cerivisiae* sold by the company LSN under the trade name Cytovitin®; and the extract of the alga *Macrocystis pyrifera* sold by the company Secma under the trade name Kelpadelie®; or on glycosaminoglycan synthesis, such as the product of fermentation of milk with *Lactobacillus vulgaris*, sold by the company Brooks under the trade name Biomin yogourth®; the extract of the brown alga *Padina pavonica* sold by the company Alban Muller under the trade name HSP3; and the extract of *Saccharomyces cerevisiae* available especially from the company Silab under the trade name Firmalift® or from the company LSN under the trade name Cytovitin®; or on fibronectin synthesis, such as the extract of the zooplankton Salina sold by the company Seporga under the trade name GP4G®; the yeast extract available especially from the company Alban Muller under the trade name Drieline®; and the palmitoyl pentapeptide sold by the company Sederma under the trade name Matrixil®; or on the inhibition of metalloproteases (MMPs), such as, more particularly, MMP 1, 2, 3 or 9. Mention may be made of: retinoids and derivatives, oligopeptides and lipopeptides, lipoamino acids, the malt extract sold by the company Coletica under the trade name Collalift®; extracts of blueberry or of rosemary; lycopene; isoflavones, their derivatives or plant extracts containing them, in particular extracts of soybean (sold, for example, by the company Ichimaru Pharcos under the trade name Flavosterone SB®), of red clover, of flax, of kakkon, or of sage; or on the inhibition of serine proteases such as leukocyte elastase or cathepsin G. Mention may be made of: the peptide extract of Leguminosa seeds (*Pisum sativum*) sold by the company LSN under the trade name Parelastyl®; heparinoids; and pseudodipeptides such as {2-[acetyl-(3-trifluoromethylphenyl)amino]-3-methylbutynylamino}acetic acid.

Among the active agents that stimulate epidermal macromolecules, such as fillagrin and keratins, mention may be made especially of the extract of lupin sold by the company Silab under the trade name Structurine®; the extract of beech *Fagus sylvatica* buds sold by the company Gattefosse under the trade name Gatuline®; and the extract of the zooplankton Salina sold by the company Seporga under the trade name GP4G®.

The antifungal serums of this invention can optionally further contain an agent for stimulating the proliferation of fibroblasts or keratinocytes and/or keratinocyte differentiation. The agents for stimulating the proliferation of fibroblasts that may be used in the composition according to the invention may be chosen, for example, from plant proteins or polypeptides, extracts, especially of soybean (for example an extract of soybean sold by the company LSN under the name Eleseryl SH-VEG 8 or sold by the company Silab under the trade name Raffermine®); and plant hormones such as giberrellins and cytokinins.

The agents for stimulating the proliferation of keratinocytes that may be used in the composition according to the invention especially comprise retinoids such as retinol and its esters, including retinyl palmitate; phloroglucinol; extracts of nut cakes sold by the company Gattefosse; and extracts of *Solanum tuberosum* sold by the company Sederma.

The agents for stimulating keratinocyte differentiation comprise, for example, minerals such as calcium; the extract of lupin sold by the company Silab under the trade name Photopreventine®; sodium beta-sitosteryl sulphate sold by the company Seporga under the trade name Phytocohesine®; and the extract of corn sold by the company Solabia under the trade name Phytovityl®; and lignans such as secoisolariciresinol. The composition according to the invention comprising these compounds is preferably intended to be used for preventing or treating signs of ageing of the skin.

The antifungal serums of this invention can optionally further contain a dermo-decontracting agent. The dermo-decontracting agents that may be used in the antifungal serums of this invention include alverine and its salts, manganese gluconate, Diazepam, the hexapeptide argireline R sold by the company Lipotec, certain carbonylated secondary and tertiary amines, adenosine, and also sapogenins and the natural extracts, in particular of Wild Yam, containing them.

The antifungal serums of this invention can optionally further contain agents for acting on the capillary circulation. The active agents acting on the capillary circulation (vasoprotective or vasodilating agents) may be chosen from flavonoids, ruscogenins, esculosides, escin extracted from common horse chestnut, nicotinates, heperidine methyl chalcone, essential oils of lavender or of rosemary, and extracts of *Ammi visnaga*. The amount of these active agents may vary within a wide range. In general, these active agents are present in a concentration ranging from 0.01% to 15% and preferably from 0.05% to 10% by weight relative to the total weight of the antifungal serum.

The antifungal serums of this invention can optionally further contain agents acting on the energy metabolism of cells. The active agents concerned are those acting on the energy metabolism of the skin, for instance, and in a non-limiting manner, ATP synthesis, and also those involved in the respiratory chain of the cell or in the energy reserves. Mention may be made of coenzyme Q10 (ubiquinone), cytochrome C, creatine or phosphocreatine.

This invention is illustrated by the following examples that are merely for the purpose of illustration and are not to be regarded as limiting the scope of the invention or the manner in which it can be practiced. Unless specifically indicated otherwise, parts and percentages are given by weight.

EXAMPLE 1

In this experiment an antifungal serum of this invention was prepared by adding 25 ml of jojoba oil (filtered and unrefined), 25 ml of peppermint oil, 25 ml of tea tree oil, 25 ml of isoamyl lactate, and 25 ml of undecylenic acid to a 250 ml beaker. Then, the mixture of liquids were well mixed with a stifling rod to make the antifungal serum.

The antifungal serum was subsequently used to treat the toenail of a 59 year old male who was suffering from onychomycosis. The onychomycosis was the result of trauma caused by stubbing the big toe of the patient on a bed post. In this case, the onychomycosis was black in appearance and was located under the toenail. The antifungal serum was brushed onto the infected toe of the patient every morning, in the early afternoon, and in the evening every day.

After about one week of treatment the black color of the fungus lightened and the toenail returned to a relatively normal appearance. The application of the antifungal serum was continued in the morning and in the evening for about 6 months to allow the infected toenail to completely grow out leaving only a normal nail structure. There was no reoccurrence of the onychomycosis after another 6 months. In other words, the patient remained free of fungus for 6 months after discontinuing treatment with the antifungal serum.

EXAMPLE 2

An antifungal serum was made as described in Example 1 and was subsequently used to treat a patient with Down's Syndrome who had been suffering from onychomycosis for many years. All ten of toes of this 30 year old male subject were severely infected with onychomycosis. In any case, the antifungal serum was applied to the toenails of the patient at least twice every day. After about 6 months of treatment the onychomycosis was completely eliminated from all of the toes of this patient. However, onychomycosis did reoccur and treatment was resumed on the infected toes. The subsequent treatment again eliminated the onychomycosis after several months of further treatment.

EXAMPLE 3

An antifungal serum was made as described in Example 1 and was subsequently used to treat a patient with diabetes mellitus who had been suffering from onychomycosis for many years. All ten of toes of this 65 year old male subject were severely infected with onychomycosis. In any case, the antifungal serum was applied to the toenails of the patient at least twice every day. After about 6 months of treatment the onychomycosis was completely eliminated from all of the toes of this patient. There was no reoccurrence of the onychomycosis after another 2 months. In other words, the patient remained free of fungus for 2 months after discontinuing treatment with the antifungal serum.

EXAMPLE 4

An antifungal serum was made as described in Example 1 and was subsequently used to treat a 75 year old female patient that was otherwise healthy who had been suffering from onychomycosis for about 6 months. She had previously treated the onychomycosis which several over the counter products without success. Most of her toes were severely infected with the onychomycosis. In any case, the antifungal serum was applied to the toenails of the patient at least twice every day. After about 6 months of treatment the onychomycosis was completely eliminated from all of the toes of this patient. There was no reoccurrence of the onychomycosis after another 6 months. In other words, the patient remained free of fungus for 6 months after discontinuing treatment with the antifungal serum.

EXAMPLE 5

An antifungal serum was made as described in Example 1 and was subsequently used to treat a 55 year old female patient that was otherwise healthy who had been suffering from onychomycosis for over 2 years. She had previously treated the onychomycosis which several over the counter products without success. Most of her toes were severely infected with the onychomycosis. In any case, the antifungal serum was applied to the toenails of the patient at least twice every day. After about 6 months of treatment the onychomycosis was completely eliminated from all of the toes of this patient. There was no reoccurrence of the onychomycosis after another 6 months. In other words, the patient remained free of fungus for 6 months after discontinuing treatment with the antifungal serum.

EXAMPLE 6

An antifungal serum was made as described in Example 1 and was subsequently used to treat 22 patients of a dermatologist who were diagnosed by the dermatologist as having onychomycosis on at least one of their toes. All of the 22 patients showed significant improvement within 2 months of starting treatment by applying the antifungal serum to the infected areas at least once a day. All of the patients in this study were satisfied with the results of their treatments and the onychomycosis was completely eliminated in the case of 4 of the patients after 6 months of treatment.

While certain representative embodiments and details have been shown for the purpose of illustrating the subject invention, it will be apparent to those skilled in this art that various changes and modifications can be made therein without departing from the scope of the subject invention.

What is claimed is:

1. An antifungal serum which is comprised of (1) an alkyl lactate, wherein the alkyl group in the alkyl lactate contains from 4 to about 6 carbon atoms, (2) *Simmondsia chinesis* seed oil, and (3) undecylenic acid.

2. An antifungal sultan as specified if claim 1 wherein the alkyl lactate is isoamyl lactate.

3. An antifungal serum as specified in claim 1 wherein the *Simmondsia chinesis* seed oil is golden *Simmondsia chinesis* seed oil.

4. An antifungal serum as specified in claim 1 wherein the *Simmondsia chinesis* seed oil is filtered.

5. An antifungal serum as specified in claim 1 wherein the *Simmondsia chinesis* seed oil is refined.

6. An antifungal serum as specified in claim 1 wherein the isoamyl lactate is present at a level which is within the range of about 5 weight percent to about 80 weight percent, wherein the *Simmondsia chinesis* seed oil is present at a level of about 5 weight percent to about 80 percent, and wherein the undecylenic acid is present at a level of about 0.25 weight percent to about 40 weight percent.

7. An antifungal serum as specified in any of claim 1 wherein the isoamyl lactate is present at a level which is within the range of about 15 weight percent to about 40 weight percent, wherein the *Simmondsia chinesis* seed oil is present at a level of about 15 weight percent to about 40 percent, and wherein the undecylenic acid is present at a level of about 20 weight percent to about 25 weight percent.

8. An antifungal serum as specified in claim 7 wherein the antifungal serum is further comprised of at least one additional oil which is selected from the group consisting of vegetable oil, peppermint oil, and tea tree oil.

9. An antifungal serum as specified in claim 8 wherein the additional oil is a vegetable oil.

10. An antifungal serum as specified in claim 9 wherein the additional oil is peppermint oil.

11. An antifungal serum as specified in claim 9 wherein the additional oil is tea tree oil.

12. An antifungal serum as specified in claim 9 wherein additional oil is a combination of peppermint oil and tea tree oil, wherein the peppermint oil is present at a level which is within the range of about 5 weight percent to about 45 weight percent, and wherein the peppermint oil is present at a level which is within the range of about 5 weight percent to about 45 weight percent.

13. An antifungal serum as specified in claim 1 wherein the antifungal serum is further comprised of peppermint oil and tea tree oil, wherein the alkyl lactate is isoamyl lactate, wherein the isoamyl lactate is present at a level which is within the range of about 15 weight percent to about 25 weight percent, wherein the *Simmondsia chinesis* seed oil is present at a level of about 15 weight percent to about 25 weight percent, wherein the undecylenic acid is present at a level with is within the range of about 20 weight percent to about 30 weight percent, wherein the peppermint oil is present at a level which is within the range of about 15 weight percent to about 25 weight percent, and wherein the tea tree oil is present in the at a level which is within the range of about 15 weight percent to about 25 weight percent.

14. An antifungal serum as specified in claim 1 wherein the antifungal serum is further comprised of peppermint oil and tea tree oil, wherein the alkyl lactate is isoamyl lactate, wherein the isoamyl lactate is present at a level which is within the range of about 18 weight percent to about 22 weight percent, wherein the *Simmondsia chinesis* seed oil is present at a level of about 18 weight percent to about 22 weight percent, wherein the undecylenic acid is present at a level with is within the range of about 23 weight percent to about 27 weight percent, wherein the peppermint oil is present at a level which is within the range of about 18 weight percent to about 22 weight percent, and wherein the tea tree oil is present in the at a level which is within the range of about 18 weight percent to about 22 weight percent.

15. A method for treating a human fingernail or toenail which is infected with onychomycosis which comprises applying the antifungal serum specified in claim 1 to the infected nail.

16. The method as specified in claim 15 wherein the antifungal serum is applied at least once a day.

17. A method for treating a human fingernail or toenail which is infected with onychomycosis which comprises applying the antifungal serum specified in claim 6 to the infected nail.

18. A method for treating a human fingernail or toenail which is infected with onychomycosis which comprises applying the antifungal serum specified in claim 7 to the infected nail.

19. A method for treating a human fingernail or toenail which is infected with onychomycosis which comprises applying the antifungal serum specified in claim 13 to the infected nail.

20. A method for treating a human fingernail or toenail which is infected with onychomycosis which comprises applying the antifungal serum specified in claim 14 to the infected nail.

* * * * *